United States Patent [19]
Skold et al.

[11] Patent Number: 5,451,507
[45] Date of Patent: * Sep. 19, 1995

[54] METHOD FOR IMMUNOCHROMATOGRAPHIC ANALYSIS

[75] Inventors: Carl N. Skold, Mountain View; Armen B. Shanafelt, Redwood City; Vartan Ghazarossian, Menlo Park; Edwin F. Ullman, Atherton, all of Calif.

[73] Assignee: Syntex (U.S.A.) Inc., Palo Alto, Calif.

[*] Notice: The portion of the term of this patent subsequent to Aug. 2, 2011 has been disclaimed.

[21] Appl. No.: 241,307

[22] Filed: May 10, 1994

Related U.S. Application Data

[60] Continuation of Ser. No. 940,137, Sep. 3, 1992, Pat. No. 5,334,513, which is a division of Ser. No. 376,723, Jul. 7, 1989, Pat. No. 5,164,294, which is a continuation-in-part of Ser. No. 194,708, May 17, 1988, Pat. No. 5,039,607.

[51] Int. Cl.$^6$ .......................................... G01N 33/558
[52] U.S. Cl. ................................... 435/7.92; 422/56; 435/4; 435/7.93; 435/805; 435/970; 436/161; 436/162; 436/501; 436/514; 436/518
[58] Field of Search ................. 422/56; 435/4, 7.92, 435/7.93, 805, 970; 436/161, 162, 501, 514, 518

[56] References Cited

U.S. PATENT DOCUMENTS

| | | | |
|---|---|---|---|
| 3,011,874 | 12/1961 | Deutsch | 435/805 X |
| 3,646,346 | 2/1972 | Catt | 250/83 |
| 3,654,090 | 4/1972 | Schurrs et al. | 195/103.5 |
| 3,791,932 | 2/1974 | Schurrs et al. | 195/103.5 |
| 3,817,837 | 6/1974 | Rubenstein et al. | 195/103.5 |
| 3,966,879 | 6/1976 | Renn et al. | 195/103.5 |
| 3,990,850 | 11/1976 | Friedman et al. | 23/230 B |
| 3,996,345 | 12/1976 | Ullman et al. | 424/12 |
| 4,055,394 | 10/1977 | Friedman et al. | 23/253 TP |
| 4,062,733 | 12/1977 | Edwards et al. | 195/103.7 |
| 4,067,959 | 1/1978 | Bolz | 424/1 |
| 4,094,647 | 6/1978 | Deutsch et al. | 23/253 TP |
| 4,104,029 | 8/1978 | Maier, Jr. | 23/230 B |
| 4,108,729 | 8/1978 | Mennen | 195/127 |
| 4,120,945 | 10/1978 | Gutcho et al. | 424/1 |
| 4,160,008 | 7/1979 | Fenocketti et al. | 422/56 |
| 4,160,645 | 7/1979 | Ullman | 23/230 B |
| 4,168,146 | 9/1979 | Grubb et al. | 23/230 B |
| 4,189,304 | 2/1980 | Adams, Jr. et al. | 23/230 B |
| 4,220,450 | 9/1980 | Maggio | 23/230 |
| 4,233,402 | 11/1980 | Maggio et al. | 435/7 |
| 4,287,300 | 9/1981 | Gibbons et al. | 435/5 |
| 4,298,688 | 11/1981 | Kallies | 435/14 |
| 4,327,073 | 4/1982 | Huang | 424/1 |
| 4,366,241 | 12/1982 | Tom et al. | 435/7 |
| 4,384,958 | 5/1983 | Wisebaker et al. | 210/658 |
| 4,425,438 | 1/1984 | Bauman et al. | 436/527 |

(List continued on next page.)

FOREIGN PATENT DOCUMENTS

0314499A1 5/1989 European Pat. Off. .
WO86/04683 8/1986 WIPO .

*Primary Examiner*—David Saunders
*Attorney, Agent, or Firm*—Theodore J. Leitereg; Janet K. Kaku

[57] ABSTRACT

Methods are disclosed for conducting assays. One such method comprises providing in combination a first bibulous member zone ("first zone") and a liquid medium containing a component. The first zone has non-diffusively bound thereto a reagent interreactive with the component. Conditions are selected wherein the liquid medium and at least a portion of the component contained therein traverse all of the first zone and migrate by capillary migration into a second bibulous member zone ("second zone"). The second zone is of a different composition than the first zone and is incapable of specifically binding the component except when an analyte is to be detected and the method further includes causing a reagent to become bound to the first bibulous member zone in relation to the amount of analyte present. The distance the component has migrated into the second zone or the difference in the distances the medium and the component have migrated into the second zone is determined, the distance or the difference being related to the amount of the component in the liquid medium or the amount of the reagent.

10 Claims, 1 Drawing Sheet

U.S. PATENT DOCUMENTS

| | | | |
|---|---|---|---|
| 4,434,236 | 2/1984 | Freytag | 436/512 |
| 4,435,504 | 3/1984 | Zuk et al. | 435/7 |
| 4,438,067 | 3/1984 | Siddiqi | 422/56 |
| 4,551,426 | 11/1985 | Freytag et al. | 435/7 |
| 4,703,003 | 10/1987 | Struck | 435/68 |
| 4,744,952 | 5/1988 | Ogita | 422/56 |
| 4,826,759 | 5/1989 | Guire et al. | 435/4 |
| 4,861,711 | 8/1989 | Friesen et al. | 436/574 X |
| 4,868,108 | 9/1989 | Bahar et al. | 435/7 |
| 4,883,764 | 11/1989 | Kloepfer | 436/63 |
| 4,959,324 | 9/1990 | Ramel et al. | 436/169 |
| 4,973,549 | 11/1990 | Khanna et al. | 435/11 |
| 4,999,287 | 3/1991 | Allen et al. | 435/11 |
| 5,334,513 | 8/1994 | Skold et al. | 435/7.92 |

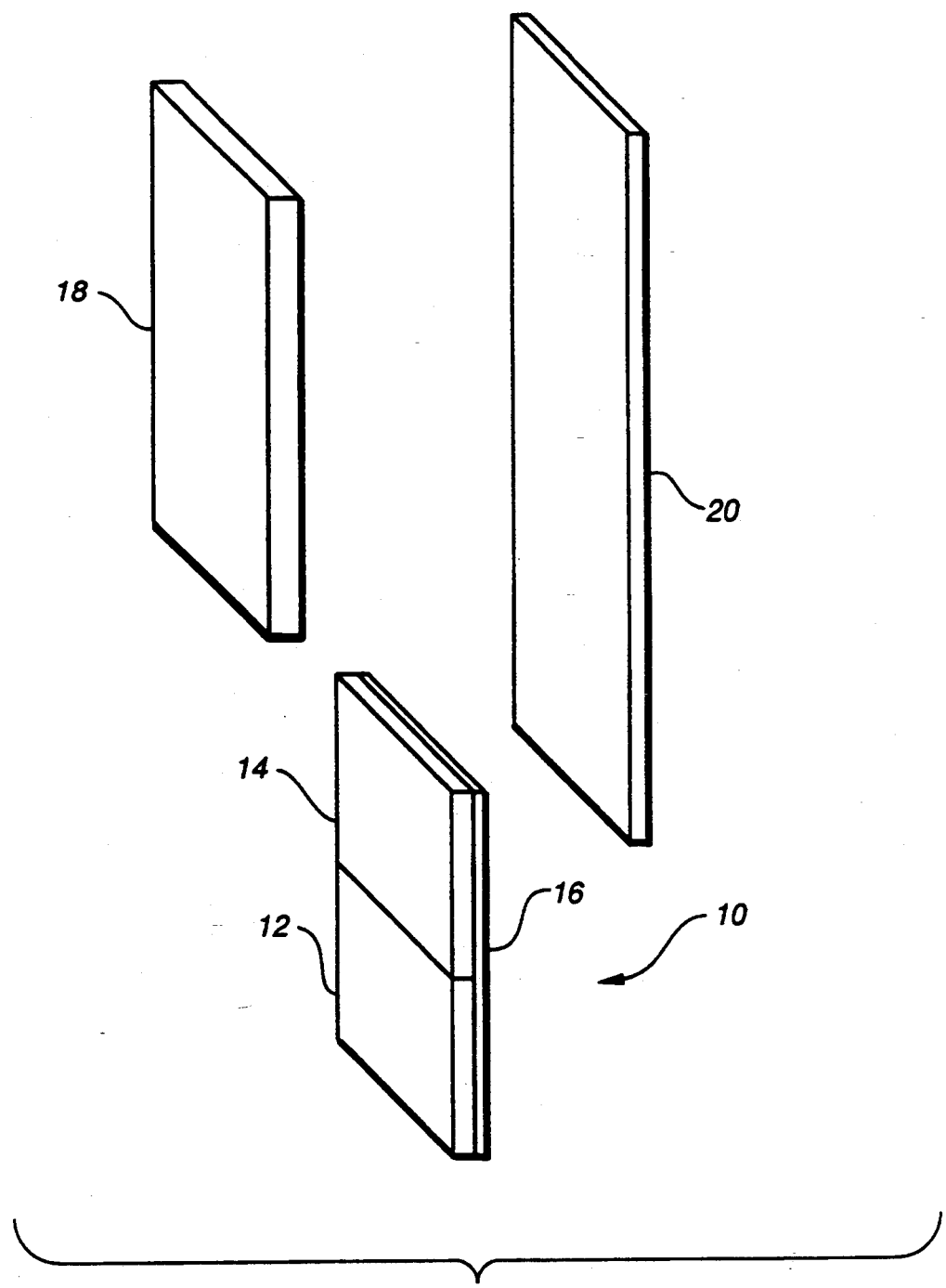
FIG._1

METHOD FOR IMMUNOCHROMATOGRAPHIC ANALYSIS

CROSS-REFERENCE TO RELATED APPLICATION

This is a continuation of application Ser. No. 07/940,137, filed Sep. 3, 1992, now U.S. Pat. No. 5,334,513, which in turn is a divisional of application Ser. No. 07/376,723, filed Jul. 7, 1989, now U.S. Pat. No. 5,164,294, which in turn is a continuation-in-part of application Ser. No. 07/194,708, filed May 17, 1988, now U.S. Pat. No. 5,039,607, the disclosure of which is incorporated herein by reference in its entirety.

BACKGROUND OF THE INVENTION

1. Field of the Invention

The ability to employ naturally occurring receptors or antibodies directed to specific compounds in assaying for the presence of a compound of interest has created a burgeoning immunoassay business. In each of the assays, complementary pair of specific binding pair ("sbp") members, usually an immunological pair, involving a ligand and a receptor (antiligand) is involved, wherein one of the sbp members is labeled with a label which provides a detectable signal. The immunoassay methodology results in a distribution of the signal label between signal label bound in a complex of the sbp members and unbound signal label. The differentiation between bound and unbound signal label can be as a result of physical separation of bound from unbound signal label or modulation of the detectible signal between bound and unbound signal label.

For the most part, immunoassays have been directed to quantitative determination of a wide variety of compounds of interest in clinical laboratories requiring relatively sophisticated equipment and careful technique. Immunoassays have found less extensive commercial application where semi-quantitative or qualitative results would be acceptable and the determination would involve non-laboratory personnel, such as in a home or a medical practitioner's office. Even in the clinical laboratory, simple and rapid screening tests employing inexperienced personnel could serve to provide substantial economies.

In developing an immunoassay, there are many considerations. One consideration is to provide substantial differentiation between the observed signal resulting from signal label when bound as compared to unbound. Another consideration is to minimize interference from endogenous materials in the sample suspected of containing the compound of interest. A further consideration is the ease with which the observed signal can be detected and serve to differentiate between concentrations in the concentration range of interest. Another consideration is the concentration of the compound of interest in a sample. Other factors include the ease of preparation of the reagents, the precision with which samples and reagent solutions must be prepared and measured, the storage stability of the reagents, the number of steps required in the protocol, and the proficiency and accuracy with which each of the steps must be performed. Therefore, in developing an assay that can have application with untrained personnel, such as assays to be performed in the home, in forensic medicine, by medical practitioners, or the like, the observed result should be minimally affected by variations in the manner in which the protocol is carried out and the techniques for performing the various steps should be simple.

In general, immunoassays that permit the determination of a dilute analyte in a sample have been difficult to design and those that have been demonstrated require numerous steps and long periods of time.

Frontal analysis (or breakthrough analysis) is a known method for quantitating active groups on a solid support in a chromatography column (C. R. Lowe and P. D. G. Dean, *Affinity Chromatography*, John Wiley & Sons, Ltd., New York, 1974). In frontal analysis, a solution of the reacting species at a known concentration is applied to the column. Measurement of the volume needed to saturate the column so that the reacting species is detected in the column effluent (the breakthrough volume) allows determination of the active group concentration on the column.

2. Description of the Related Art

U.S. Pat. No. 4,425,438 describes a method and device for assaying a test substance utilizing a primary absorbent substance for selectively allowing only a quantity of an analytical reagent proportional to the quantity of test substance to pass therethrough when test substance and analytical reagent are contacted with the primary absorbent. An analytical absorbent is disposed in a series of zones for sequentially absorbing the analytical reagent which passes through the primary absorbent so that detection of the last zone of absorbed analytical reagent indicates the quantity of test substance. In the method test substance and analytical reagent are passed through the primary absorbent and then the analytical absorbent followed by detection of the last zone in which analytical reagent is absorbed. The device is a funnel with the primary absorbent therein for directing the test substance and analytical reagent to a narrow tube holding the analytical absorbent.

A test device for determining a characteristic of a sample, particularly for determining substances in fluid samples, is disclosed in U.S. Pat. No. 4,094,647. A thin layer chromatography device and method of making a chromatography test is disclosed in U.S. Pat. No. 4,384,958. An immunoassay wherein labeled antibody is displaced from immobilized analyte analog is described in U.S. Pat. No. 4,434,236. A device and method for detecting myoglobin is disclosed in U.S. Pat. No. 4,189,304. Test strips for analyzing substances dissolved in liquids are described in U.S. Pat. No. 4,438,067. A multi-layered test device for determining the presence of a liquid sample component and the method of using such a device, are described in U.S. Pat. No. 4,160,008. A method for measuring antigen by labeled antigen using insoluble antibody is disclosed in Japanese Patent Application Laid-Open No. 5925/73 Jan. 25, 1973.

A concentrating zone method in heterogeneous immunoassays is disclosed in U.S. Pat. No. 4,366,241. U.S. Pat. No. 4,168,146 describes an immunoassay test strip. U.S. Pat. Nos. 3,990,850 and 4,055,394 describe diagnostic test cards. An automated method for quantitative analysis of biological fluids is described in U.S. Pat. No. 4,327,073. A chromogenic support immunoassay is disclosed in International Application No. PCT/US83/01887. A heterogeneous immunoassay for digoxin using ouabain as a separation means is described in U.S. Pat. No. 4,551,426.

A wide variety of patents and patent applications provide an extensive literature of different techniques for producing detectible signals in immunoassays. The following list is merely illustrative of some of these techniques which can find application in this invention. The following is a list of United States patents and patent applications and a general statement of the type of label involved:

U.S. Pat. Nos. 3,646,346, Radioactive Label; 3,654,090, 3,791,932 and 3,817,838, Enzyme Labels; 3,996,345, Fluorescer-Quencher Labels; 4,062,733, Radioactive Label; 4,067,959, Fluorescer or Enzyme Label; 4,104,029, Chemiluminescent Label; and 4,160,645, Non-Enzymatic Catalyst Label. See U.S. Pat. No. 3,966,879 for an electrophoretic technique employing an antibody zone and U.S. Pat. No. 4,120,945 for an RIA where labeled analyte is initially bound to a solid support through antibody. U.S. Pat. No. 4,233,402 employs enzyme pair labels; U.S. Pat. No. 4,720,450, chemically induced fluorescent labels; and U.S. Pat. No. 4,287,300, enzyme anionic charge labels.

SUMMARY OF THE INVENTION

The methods of the present invention are useful in conducting assays. One such method for conducting an assay comprises providing in combination a first bibulous member zone ("first zone") and a liquid medium containing a component. The first zone has non-diffusively bound thereto a reagent interreactive with the component. Conditions are utilized wherein the liquid medium and at least a portion of the component contained therein traverse all of the first zone and migrate into a second bibulous member zone ("second zone") by capillary migration. The second zone is of different composition than that of the first zone and is incapable of specifically binding the component except when an analyte is to be detected and the method further includes causing a reagent to become bound to the first bibulous member zone in relation to the amount of analyte present. The distance the component has migrated into the second zone or the difference in the distances the medium and the component have migrated into the second zone is determined. The distance or the difference is related to the amount of the component in the liquid medium or the amount of the reagent.

Another such method for determining the amount of a component in a liquid medium, comprises contacting a first bibulous member zone ("first zone") with a liquid medium containing a component. The first zone has non-diffusively bound therein a reagent interreactive with the component. The contact is carried out under conditions wherein the liquid medium and at least a portion of the component contained therein traverse all of the first zone and migrate into a second bibulous member zone ("second zone") by capillary migration. The second zone is of different composition than the first zone and is incapable of specifically binding the component except when an analyte is to be detected and the method further includes causing a reagent to become bound to the first bibulous member zone in relation to the amount of analyte present. The second zone may be chemically reactive with the component. The distance the component has migrated into the second zone or the difference in the distance the medium and the component have migrated into the second zone is measured. The distance or the difference is related to the amount of the component in the liquid medium.

Another such method for conducting an assay comprises combining a solution of an analyte with a first bibulous member wherein a reagent capable of reacting with the analyte becomes non-diffusively bound to the first bibulous member. A liquid medium containing a component is combined with the first bibulous member wherein the component interreacts with the reagent. The first bibulous member is in liquid receiving relationship with, or is a spacially separated portion of, a second bibulous member of different composition than that of the first bibulous member and incapable of specifically binding the reagent. Conditions are chosen wherein the liquid medium and the component first traverse the first bibulous member and then at least a portion of the second bibulous member by capillary action. A border defined by the concentration of the component, or a reaction product thereof, on the second bibulous member is determined. The position of the border is related to the amount of analyte in the solution or the amount of reagent on the first bibulous member.

Another such method is useful in assaying for the presence of an analyte in a sample suspected of containing the analyte. In one embodiment of the method of the present invention, a portion of a first bibulous member is contacted with a first liquid, usually aqueous, medium or solution containing a first reagent such as a specific binding pair (sbp) member to cause the first reagent to become bound to the first bibulous member. The first bibulous member can be in, or be placed in, liquid receiving relationship with an absorbent member. If the first bibulous member is in liquid receiving relationship with the second bibulous member prior to contact of the first bibulous member with the first medium, then the first reagent must be capable of binding to the analyte to form bound and unbound portions of the first reagent, wherein the unbound portion is the first reagent in the first medium. The first reagent is then caused to become bound to the first bibulous member. The contact is carried out under conditions wherein the first medium traverses or flows through the first bibulous member and at least a portion of the absorbent member by capillary action. Next, the first bibulous member is brought into liquid receiving relationship with a second bibulous member if it is not already in such a relationship. A portion of the first bibulous member is contacted with the second liquid, usually aqueous, medium under conditions wherein the second aqueous medium traverses the first bibulous member by capillary action and at least a portion of the second bibulous member. In this way a component in the second medium is absorbed by and preferably becomes non-diffusely bound to the second bibulous member in relation to the presence of analyte in the first medium. The presence of the component on at least a portion of the second bibulous member is determined and is indicative of the presence of analyte. Furthermore, the distance the component traverses the second bibulous member is related to the amount of analyte in the first medium.

In another aspect of the present invention a combination is provided in a first liquid, usually aqueous, medium or solution. The combination includes (1) at least a portion of a first bibulous member, at least a portion thereof having a first reagent, for example, an sbp member, non-diffusively bound thereto, and (2) a sample suspected of containing an analyte. When the analyte is not capable of binding to the first reagent, a second reagent capable of binding to the analyte and to the first reagent is present in the medium or on the first bibulous member. The first bibulous member is in liquid receiving relationship with an absorbent member. Conditions are chosen such that the first medium or solution traverses or flows through the first bibulous member and at least a portion of the absorbent member by capillary action. The first bibulous member is then brought into liquid receiving relationship with a second bibulous member. Another combination is provided in a second liquid, usually aqueous, medium. This combination includes at least a portion of the first bibulous member and a component that is capable of binding to the first or second reagent in relation to the presence of the analyte in the first medium. The second bibulous member preferably has a specific binding partner for the component non-diffusively bound to at least a portion thereof. The combination is provided under conditions wherein the second liquid medium traverses at least a portion of the first bibulous member and at least a portion of the second bibulous member by capillary action. The distance the component traverses the second bibulous member is determined and is related to the amount of analyte in the sample.

In another aspect of the present invention, the liquid receiving relationship between the first bibulous member and an absorbent member is terminated prior to bringing the first bibulous member into contact with a second bibulous member.

In another embodiment of the present invention, the second bibulous member is a chromatographic member such as an immunochromatographic member and a border is determined on the chromatographic member. The position of the border is related to the amount of analyte in the first medium or the amount of component in the liquid medium or the amount of reagent on the first bibulous member.

Another aspect of the present invention concerns a method for conducting an assay for an analyte, wherein there is provided in combination in a first liquid, usually aqueous, medium (1) a portion of a bibulous member to at least a portion of which is non-diffusively bound a fist specific binding pair (sbp) member and (2) a sample suspect of containing an analyte. A first reagent may include a conjugate comprising a second sbp member capable of binding the analyte and a third spb member complementary to the first sbp member, which is present in the medium or on the bibulous member. The bibulous member is in liquid receiving relationship with an absorbent member. The first medium traverses the bibulous member and at least a portion of the absorbent member by capillary action and the conjugate becomes non-diffusively bound to the bibulous member. The liquid receiving relationship between the bibulous member and the absorbent member is terminated. Another combination is provided in a second liquid, usually aqueous, medium, which includes a portion of the first bibulous member and a component. The component comprises an analyte analog bound to, or capable of becoming bound to, a member of a signal producing system. The bibulous member is in liquid receiving relationship with an immunochromatographic member having non-diffusively bound thereto a binding partner for the component. Under the conditions employed, the second medium traverses the bibulous member and at least a portion of the immunochromatographic member by capillary action. The bibulous member is in liquid receiving relationship with the absorbent member and the immunochromatographic member at substantially different times. A border is determined on the immunochromatographic member, wherein the position of the border is related to the amount of analyte in the first medium.

Another aspect of the present invention concerns a method for conducting an assay for an analyte, wherein there is provided in combination in a first liquid, usually aqueous, medium or solution (1) a portion of a first bibulous member to which is non-diffusively bound a first reagent such as, for example, an analyte analog, and (2) a sample suspected of containing an analyte. A second reagent capable of binding said analyte is present in the solution or on the bibulous member. The bibulous member is in liquid receiving relationship with an absorbent member. The first medium or solution traverses or flows through the bibulous member and at least a portion of an absorbent member by capillary action and the second reagent becomes non-diffusively bound to the bibulous member in inverse proportion to the amount of the analyte in the first medium or solution. The liquid receiving relationship between the bibulous member and said absorbent member is terminated. Another combination is provided in a second liquid, usually aqueous, medium, which includes a portion of said bibulous member and a component. The component includes, or is capable of having bound to it, a member of a signal producing system, and is capable of binding to the first or second reagent bound to the bibulous member. The bibulous member is in liquid receiving relationship with an immunochromatographic member having non-diffusively bound thereto a specific binding partner for the component. Under the conditions employed, the second medium traverses the bibulous member and at least a portion of the immunochromatographic member by capillary action. The bibulous member is in liquid receiving relationship with the absorbent member and the immunochromatographic member at substantially different times. A border is determined on the immunochromatographic member, wherein the position of the border is related to the amount of analyte in the first medium.

In another embodiment a combination is provided comprising (1) a bibulous member to which is non-diffusively bound an antibody for an analyte, and (2) a first liquid, usually aqueous, medium or solution suspected of containing an analyte. The bibulous member is in liquid receiving relationship with an absorbent member. Conditions are chosen to allow the first medium to traverse the bibulous member and at least a portion of the absorbent member by capillary action. The liquid receiving relationship between said bibulous member and the absorbent member is terminated. Another combination is provided in a second liquid, usually aqueous, medium that includes a portion of the bibulous member and a component. The component is bound to, or capable of becoming bound to, a member of a signal producing system and is capable of binding to the antibody for said analyte. The bibulous member is in liquid receiving relationship with an immunochromatographic member having non-diffusively bound thereto a specific binding partner for the component. Under the conditions of the method the second medium traverses the bibulous member and at least a portion of the immunochromatographic member by capillary action, with the proviso that the bibulous member is in liquid receiving relationship with the absorbent member and the immunochromatographic member at substantially different times. A border is determined on the immunochromatographic member. The position of the border is related to the amount of analyte in the first medium or solution, the amount of reagent, or the amount of component in the second medium.

Another aspect of the present invention concerns a method for conducting an assay for digoxin. The method comprises contacting an end portion of a bibulous strip having a zone distal from the end portion, wherein the zone has an antibody ($Ab_1$) for an organic molecule of molecular weight less than 1500 non-diffusively bound thereto, with a first aqueous medium or solution suspected of containing digoxin. A conjugate comprising an antibody for digoxin conjugated or bound to the organic molecule is present in the first medium or on the bibulous strip. Under the conditions chosen the first medium or solution traverses by capillary action the bibulous strip and at least a portion of an absorbent member in liquid receiving relationship with the strip and the conjugate becomes non-diffusively bound to $Ab_1$, and digoxin, if present, becomes bound to the conjugate. The liquid receiving relationship between the bibulous member and the absorbent member is terminated. A combination is provided in a second liquid, usually aqueous, medium that comprises the end portion of the bibulous strip and a component comprising a digoxin analog bound to an enzyme. The bibulous strip is in liquid receiving relationship with an immunochromatographic strip having non-diffusively bound thereto an antibody for digoxin. The second medium is allowed to traverse the bibulous strip and at least a portion of the immunochromatographic member by capillary action, with the proviso that the strip is in liquid receiving relationship with the absorbent member and the immunochromatographic strip at substantially different times. Again, a border on the immunochromatographic strip is determined wherein the position of the border is related to the amount of analyte in said sample.

In another embodiment of an assay for digoxin, an end portion of a bibulous strip to which is non-diffusively bound a digoxin analog is contacted with a first liquid, usually aqueous, medium or solution containing a sample suspected of containing digoxin. An antibody for digoxin ($Ab_D$) is present in the first medium or on the bibulous strip. The bibulous strip is in liquid receiving relationship with an absorbent member and conditions are chosen wherein the first medium traverses the bibulous member and at least a portion of the absorbent member by capillary action and the antibody $Ab_D$ becomes non-diffusively bound to the digoxin analog when digoxin is not present in the sample. The liquid receiving relationship between the bibulous strip and the absorbent member is terminated. A combination is provided in a second liquid, usually aqueous, medium and includes the end portion of the bibulous strip and a conjugate comprising an antibody for $Ab_D$ bound to an enzyme. The bibulous strip is in liquid receiving relationship with an immunochromatographic strip having non-diffusively bound thereto a receptor for the antibody for $Ab_D$. Under the conditions of the assay, the second medium traverses the bibulous strip and at least a portion of the immunochromatographic strip by capillary action. The bibulous strip is in liquid receiving relationship with the absorbent member and the immunochromatographic strip at substantially different times. A border is determined on the immunochromatographic strip. The position of the border is related to the amount of analyte in the first medium.

In another embodiment of a method in accordance with the invention, an end portion of a bibulous member to which is non-diffusively bound an antibody for digoxin is contacted with a first aqueous medium or solution containing a sample suspected of containing digoxin. The bibulous strip is in liquid receiving relationship with an absorbent member and conditions are chosen such that the first medium traverses the bibulous member and at least a portion of the absorbent member by capillary action. The liquid receiving relationship between the bibulous member and the absorbent member is terminated. In a second liquid, usually aqueous, medium a combination of the end portion of the bibulous strip and a conjugate comprising a digoxin analog bound to an enzyme is formed. The bibulous strip is in liquid receiving relationship with an immunochromatographic strip having a receptor for conjugate non-diffusively bound thereto. The second medium traverses the bibulous strip and at least a portion of the immunochromatographic strip by capillary action. The bibulous strip is in liquid receiving relationship with the absorbent member and the immunochromatographic strip at substantially different times. Again, a border on said immunochromatographic strip is determined, the position of which is related to the amount of analyte in said first medium.

The invention further includes a device for analyzing for the presence or amount of an analyte, a reagent, or a component in a liquid medium. The device comprises a first bibulous member, an absorbent member, and a second bibulous member. The bibulous member is capable of being in alternating liquid receiving relationship with the absorbent member and the second bibulous member. Kits for carrying out the methods of the present invention are also included in the present invention.

BRIEF DESCRIPTION OF THE DRAWING

FIGURE 1 is a schematic of a device in accordance with the present invention.

DESCRIPTION OF THE SPECIFIC EMBODIMENTS

As mentioned above, the present invention is directed to methods, devices and kits for determining the presence or amount, at or above a predetermined minimum detectible amount, of a component in a liquid medium, a reagent, and/or an analyte in a sample suspected of containing the analyte. The present invention is particularly applicable to the determination of relatively dilute components in a medium, reagents on a surface or analytes in a sample. The present invention provides a means for avoiding sample interference and results in an enhanced sensitivity and a quicker method than those of the prior art. The present invention also provides means for greater balance between the number of analyte molecules in the sample and the number of molecules that will ultimately result in signal formation.

Before proceeding further with the description of the specific embodiments of the present invention, a number of terms will be defined.

Analyte—a compound or composition to be measured that is capable of binding specifically to a binding member such as an antibody or chelating agent, usually an antigen or drug, or a composition that is chemically reactive such as a molecule or ion capable of oxidation or reduction.

The precise nature of the antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The analytes include ligands and receptors that are characterized by having single binding sites (monovalent) or multiple binding sites (polyvalent). The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes, and the like.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecogonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular or ring members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g., $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as attopine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member")—one of two different molecules having an area on the surface or in a cavity which specifically binds to and is thereby defined as complementary with a particular spatial and polar organization of the other molecule and would be incapable of specifically binding to the other molecule if it lacked such a spatial and polar organization. The members of the specific binding pair are referred to as ligand and receptor (antiligand). These will usually be members of an immunological pair such as antigen-antibody, although other specific binding pairs such as biotin-avidin hormones-hormone receptors, nucleic acid duplexes, IgG-protein A, DNA-DNA, DNA-RNA, and the like are not immunological pairs but are included in the definition. An analyte can be, and usually is, an sbp member.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Labeled sbp member—a label, generally capable of electrochemical detection or absorption or emission of electromagnetic radiation, a catalyst, frequently an enzyme, bound to an sbp member. The labeled sbp member is generally a member of the signal producing system.

Antibody—an immunoglobin, or derivative or fragment thereof, having an area on the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Antibody for the analyte—an antibody specific for an analyte.

Analog analyte—a modified analyte or analyte analog or surrogate which can compete with the analogous analyte in binding to an sbp member, usually a receptor or antibody, the modification providing means to join the analyte analog to a label to provide a labeled sbp member. The analyte analog will usually differ from the analyte by more than replacement of a hydrogen with a bond which links the analyte analog to a hub or label, but need not. The term analyte surrogate refers to a compound having the capability of binding the antibody for the analyte. Thus, the analyte surrogate may bind to the antibody for the analyte in a manner similar to the analyte. On the other hand, the surrogate could be, for example, an antibody directed against the idiotype of an antibody to the analyte.

Bibulous member—a porous material having pores of at least 0.1 $\mu$, preferably at least 1.0 $\mu$, which is susceptible to flow through or traversal by an aqueous medium in response to capillary force. Such materials are generally hydrophilic or are capable of being rendered hydrophilic and preferably are cellulosic materials and materials derived from cellulose, such as fiber containing papers, e.g., filter paper, chromatographic paper, etc., but may include inorganic powders such as silica, magnesium sulfate, and alumina; and other natural polymeric materials, and synthetic or modified naturally occurring polymers, such as nitrocellulose, cellulose acetate, poly (vinyl chloride), polyacrylamide, cross linked dextran, agarose, polyacrylate, etc.; either used by themselves or in conjunction with other materials; ceramic materials; and the like. The bibulous member can be attached to a support. On the other hand, the bibulous member may provide its own support. The bibulous member may be polyfunctional or be capable of being polyfunctionalized to permit covalent bonding of reagents such as receptors, antibodies, chelating agents, oxidants, reductants, and the like, as well as to permit bonding of other compounds which form a part of the signal producing system.

Binding of receptors ligands, and detection agents to the bibulous member may be accomplished by well-known techniques, commonly available in the literature. See, for example, "Immobilized Enzymes," Ichiro Chibata, Halsted Press, New York (1978) and Cuatrecasas, *J. Bio. Chem.*, 245:3059 (1970).

The piece of bibulous material comprising the bibulous member can be a single structure such as a sheet cut into strips or it can be several strips or particulate material bound to a support or solid surface such as found, for example, in thin-layer chromatography and may have an absorbent pad either as an integral part or in liquid contact. The bibulous member can be comprised of several segments in liquid receiving relationship and preferably bound to a support. The bibulous member can also be a sheet having lanes thereon or capable of spotting to induce lane formulation, wherein a separate assay can be conducted in each lane.

The bibulous member can have a rectangular, circular, oval, triagonal or other shape provided that there is at least one direction of flow through or traversal of an aqueous medium by capillary migration. Other directions of traversal may occur such as in an oval or circular piece contacted in the center with the test solution. However, the main consideration is that there be at least one direction of flow. In the following discussion strips of bibulous material will be described by way of illustration and not limitation.

The support for the bibulous member, where a support is desired or necessary, will normally be water insoluble, non-porous, and rigid and usually will be of the same length and width as the bibulous member but may be larger or smaller. A wide variety of organic and inorganic materials, both natural and synthetic, and combinations thereof, may be employed provided only that the support does not interfere with the capillary action of the bibulous member, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like.

Absorbent member—any porous, hydrophilic bibulous material such as porous polymers, e.g. Porex ®, etc., paper, sponge, felt, and the like capable of absorbing liquid utilized in the method of the present invention. The absorbent member is preferably a non-swellable porous polymer. The absorbent member provides a plurality of functions. The first function is to serve as a receptacle or storage area for the fluid imbibed by the first bibulous member. A second function, which can be served but need not, is to control the rate at which the fluid traverses the first bibulous member. Where the absorbent member has a small dimension or is of a different material from the first bibulous member, it can act to control the rate at which fluid passes through the first bibulous member. By having irregular dimensions, it can further act to provide for different rates depending upon whether the sample or reagent solutions are being imbibed.

A further function for the absorbent member can be to measure the amount of liquid which is imbibed. Preferably, the absorbent member will take up a defined volume of liquid. By providing for graduations at sequential positions extending away from the first bibulous members and along the absorbent member, one can determine when the fluid front is at a certain position and removed the device from the medium. Alternatively, one can provide for dyes which will become colored upon dissolution in or contact with the fluid front to provide a clear signal that the device should be removed. For example, pH indicators could be used. Any technique which provides a clear indication of the presence of the fluid front can be employed.

In a strip format, the absorbent member will generally have a length of at least about 1.5, usually 2 cm and not more than about 30 cm, usually not more than about 20 cm. The width may vary from about 0.1 mm to about 3 cm. These dimensions are primarily for control of the rate and amount of solution imbibed and for convenience in handling and providing for ease of observation of the solvent front. The thickness will generally be about 0.1 mm to 5 mm, usually from about 0.5 to 3 mm. In a pad format, the absorbent member will generally have a thickness of 0.5 to 10 mm and an area of 25 to 150 $mm^2$.

The absorbent member may be partially or substantially completely enclosed in a protective casing, conveniently a clear or partially, or in some situations completely, opaque enclosure. The absorbent member should not directly contact the sample solution. It will usually be necessary that at least a minimum and normally a specific volume of solution containing an analyte pass through the first bibulous member. This can be best achieved by avoiding substantial contact of the absorbent member with the assay sample solution.

Depending upon the particular protocols involved and the construction of the device, the enclosure may be removable or irremovable, may encase only the absorbent member or may encase additionally the first and second bibulous members, may provide for one or more windows and will normally be of a sturdy inert impermeable material which will provide mechanical protection for the bibulous material and will not interfere with the performance of the assay. Normally an air opening will be provided to prevent the entrapment of air within the enclosure.

Label—A label may be any molecule bound to an sbp member that is required to produce a signal. In the subject invention, the label may be inert and serve solely as a binding site for a member of the signal producing means or it may spontaneously produce a detectable signal or may produce a detectable signal in conjunction with a signal producing means. The label may be isotopic or nonisotopic, preferably nonisotopic. However, an isotopic label can be preferred for achieving high sensitivity when using radio-autographic detections with photographic film.

Signal producing means—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to the strip.

Signal producing system—The signal producing system may have one or more components. The signal producing system includes all of the reagents required to produce a measurable signal which may include a label and signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers, or chromophoric indicators such as chelating agents, redox indicators, pH indicators, or the like.

The signal-producing system can include at least one catalyst as a label, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal in relation to the presence or amount of analyte in a sample.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the compound that produces a signal to provide the compounds that generates the signal.

Where two enzymes are employed, the involved reactions will be, for the most part, hydrolysis or redox reactions. In the case of hydrolysis, a derivatized dye precursor that has a hydrolytically labile bond, the hydrolytic enzyme and an enzyme that catalyzes the conversion of the released dye precursors to a dye conversion product is illustrative of this type of system. In redox reactions, a first enzyme can produce an essential oxidizing substrate required for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued Jul. 10, 1979, the appropriate portions of which are incorporated herein by reference.

Various combinations of enzymes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the bibulous material, either the first or second bibulous members, while the other enzyme can be a label conjugated to the analyte. Additionally, one or more other members of the signal producing system can be bound to the bibulous material depending on the particular signal producing system chosen or the particular protocol followed.

In some assays in order to have a detectable signal, it is necessary to provide means for amplifying the signal member produced by the presence of a label at a zone on a bibulous situs. Therefore, it will usually be preferable for the label to be a catalyst or luminescent compound or radioisotope, most preferably a catalyst. Preferably, catalysts are enzymes and coenzymes which can produce a multiplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horseradish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably, hydrolases such as alkaline phosphatase and $\beta$-galactosidase. Alternatively luciferases may be used such as firefly luciferase and bacterial luciferase.

Illustrative coenzymes which find use include MAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Liquid receiving relationship—Two bibulous members are in liquid receiving relationship when liquid can pass from one bibulous member to the other. This relationship can be either direct or indirect. A direct liquid receiving relationship can be realized by having two members in contact with one another so that liquid from one member will pass by capillary action to the other member and can be drawn from one member to another. An indirect liquid receiving relationship can be realized by having the two members in close proximity such that liquid can pass from one to the other. The two members can be separated by porous spacers that are inert and substantially non-resistant to fluid flow. On the other hand, or in conjunction with porous spacers, fluid flow-resistant members can be employed to control the rate of fluid flow between two members. Spatial orientation of the two members may be utilized to achieve a liquid receiving relationship.

Immunochromatograph—The immunochromatograph has a sbp member, either ligand or receptor, bound in a region to a bibulous support which allows for the movement of a liquid by capillarity across the region with transport of the analyte and, as appropriate, any members of the signal producing system. The sbp member is non-diffusively bound to the support, either covalently or non-covalently. The area to which the sbp member is uniformly bound is referred to as the "immunosorbing zone." In addition, one or more members of the signal producing system can be non-diffusively bound to the bibulous support, either covalently or non-covalently. Furthermore, a reactant for a label such as an enzyme substrate can be bound to the support.

Component—a molecule of interest, the amount thereof is to be determined in accordance with one aspect of the present invention. The component can be an inorganic compound such as an inorganic ion, either cation or anion, for example, metal ions including alkali metal ions such as lithium, potassium, sodium, etc., alkaline earth metal ions such as magnesium, calcium and so forth, copper, cobalt, manganese, aluminum, iron (ferrous or ferric), chromium, nickel, zinc, cadmium and so forth, and non-metal ions such as halides (chloride, bromide, fluoride, iodide, etc.), oxides, sulfides, sulfates, phosphites, phosphates, selenides, oxidized halogens such as iodates, periodates, chlorates, chlorites, and so forth. In general, any inorganic molecule for which there exists an interreactive reagent and which is spectroscopically detectable, preferably by reaction with a compound that can react with the inorganic molecule to provide a spectroscopic change that can be quantitated in accordance with the present invention.

The component may also be an organic molecule for which there exists an interreactive reagent such as a binding partner, for example, an sbp member, and which is spectroscopically detectable, preferably by reaction with a compound that can react with the organic compound to provide a spectroscopic change. The component can itself be measured in the assay or be a compound utilized in an assay for an analyte. Typical organic molecule components include enzyme substrates, such as glucose, ethanol, cholesterol, arabinitol, urea, lactates, amino acids, triglycerides, etc.; reducing agents such as ascotbate, uric acid, mercaptans, hydroquinones, etc.; oxidants such as quinones and disulfides; ligand-label conjugates; receptor-label conjugates; and so forth. It is an important feature of one aspect of the present invention that an analyte as well as a component and a reagent interreactive with the component can all be determined quantitatively.

Reagent interreactive with the component—a substance that is capable of interreacting stoichiometrically with a component either chemically or physically and is bound or is capable of becoming bound to a first bibulous member zone. Chemical interreaction means generally that the reagent is capable of transforming the component into another substance by breaking or forming chemical bonds and is thereby itself converted to a new compound. Physical interreaction means generally that the reagent interreacts stoichiometrically with the component other than chemically. For example, the reagent can be a ligand or receptor that binds specifically with the component by formation of hydrogen bonds, electrostatic interactions, hydrophobic interactions and so forth. The reagent can also be an inorganic or organic molecule. Exemplary of inorganic molecules are metallic and non-metallic ions, oxidants and reductants, transition metal halides, organomercury halides, etc. Exemplary of organic molecules are chelating agents, sbp members, diazonium salts, quinones, iodoso compounds, disulfides, iodoacetamides, hydroquinones, hydroxyanilines, benzidines, hydrazides, paraquat, etc.

The interreaction can involve oxidation or reduction such as, for example, the oxidation or reduction of inorganic molecules, direct covalent bond formation, or coordinate metal-ligand bond formation, including chelation, electrophilic or nucleophilic substitution, cycloaddition, etc.

Of different composition than the first zone—the composition of the second bibulous member or the second zone should be different from that of the first bibulous member or the first zone. The following is a description, by way of illustration and not limitation, of situations in which different composition can be realized. Other situations will be suggested to those skilled in the art. One such example occurs where the second bibulous member does not have bound to it any substance interreactive with a compound or an analyte. Another example occurs where the second bibulous member contains a substance interreactive with a component or a product produced upon reaction of a component with the reagent, which substance is different from the reagent on the first bibulous member. Another example is a situation where the reagent of the first bibulous member is also found on the second member but the concentrations of each on the members is different.

Ancillary Materials—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly, non-ionic surfactants, binding enhancers, e.g. polyalkylene glycols, or the like.

As mentioned above, one method in accordance with the present invention for conducting an assay provides in combination a first bibulous member zone ("first zone") and a liquid medium containing a component. The first zone has non-diffusively bound thereto a reagent interreactive with said component. Conditions are chosen wherein the liquid medium traverses all of the first zone and at least a portion of the component contained therein reacts with all of the reagent and therefore also traverses all of the first zone and is transported by capillary migration of the liquid medium into a second bibulous member zone ("second zone") of different composition than the first zone by capillary migration. The distance the component migrates into the second zone or the difference in the distances the liquid medium and the component migrate into the second zone is determined. The distance or the difference is related to the amount of the component in the liquid medium or the amount of the reagent. When it is desired to determine the amount of one of these substances the amount of the other substances will be predetermined and the distance of migration will be related to the distances obtained with known calibrators. The distances of migration can be detected by contacting the second zone with an appropriate detection agent, by the presence of an appropriate detection agent on, or bound to, the second zone that will produce a detectible signal on the second zone in relation to the presence of the component, or by direct detection of the component on the second zone.

The assay may be configured to measure the component concentration or the reagent concentration.

As described above, prior to the combination of the liquid medium and the first zone the reagent can be caused to non-diffusively bind to the first zone by contacting the first zone with a solution containing the reagent. The difference or the distance as defined above can then be related to the amount of the reagent in the solution. Furthermore, the amount of the reagent can then be related to the amount of an analyte in a solution of the reagent.

A novel feature of this aspect of the invention lies in the manner in which breakthrough volume as mentioned earlier is measured. The liquid which has passed through the first zone enters a second zone in which the volume taken up is related to the distance of liquid migration along the zone. After a suitable volume of liquid has entered the second zone, the border demarking the region containing the component and the region lacking a significant concentration of the component are located. Measuring the distance along the zone which liquid has migrated and the distance along the zone which the component has migrated as demarked by the border allows determination of the breakthrough volume. If the length of the second zone is the same for all assays, and the volume passed through the first zone just fills the second zone, then measurement of the migration distance, that is, the distance to the border, is sufficient for a determination of the breakthrough volume.

The distance of migration can be determined by direct detection of the component on the second zone or by contacting the second zone with an appropriate detection agent when said detection agent is not already present, which detection agent will produce a detectible signal on the second zone in relation to the presence of the component. The detection agent can be a substance that chemically interacts with the component usually to produce a visual signal such as color. The detection agent can be a member of a signal producing system. In general, detection agents will be reactive with an assay component or the product of reaction of an assay component and a reagent, and on reaction will produce a spectroscopically detectible change. Typical detection agents are chelators such as phenanthrolines, caroboxypyridones, phenols, $\beta$-diketones, etc.; oxidants such as quinones, ceric ion, manganese dioxide, periodates, chromates, disulfides, tetrazolium salts, etc.; reductants such as leuco dyes, mercaptans, thiosulfates, hydroquinones, benzidines, etc.; catalysts such as enzymes, co-enzymes, prosthetic groups, Medola blue, etc.; enzyme substrates; and so forth.

The first zone and the second zone can be integral to a single bibulous member, provided that the two zones must be related such that the liquid medium traverses the first zone prior to contacting the second zone and the two zones must have different compositions. On the other hand, the first zone can be integral to a first bibulous member and the second zone can be integral to a second bibulous member. The first zone can then, for example, be brought into liquid receiving relationship with the second zone prior to providing the combination of the first zone and the liquid medium. A convenient device for this aspect of the present invention is depicted in FIG. 1.

The component and the reagent can each be a member of the same or a different specific binding pair. For example, the component can be an enzyme labeled ligand analog and the reagent can be antibody for the ligand. The method can also include determination of the amount of an analyte which is a ligand.

As mentioned above, the component and the reagent can be chemically interreactive or physically interreactive. The method can be applied to the determination of both inorganic and organic molecules.

Another approach in this quantitative aspect of the present invention involves contacting a first bibulous member zone ("first zone") with a liquid medium containing a component. The first zone has non-diffusively bound therein a reagent interreactive with the component. Contacting occurs under conditions wherein the liquid medium and at least a portion of the component contained therein traverse all of the first zone and migrate into a second bibulous member zone ("second zone") of different composition than the first zone by capillary migration. Measuring the distance the component has migrated into said second zone or the difference in the distances the medium and the component have migrated into the second zone, allows the determination of the amount of the component in the liquid medium.

Another approach in accordance with this aspect of the invention involves combining a solution of an analyte with a first bibulous member wherein a reagent capable of reacting with the analyte is or becomes non-diffusively bound to the bibulous member. Next, a liquid medium containing a component is combined with the first bibulous member wherein the component is interreactive with the reagent. The first bibulous member is in liquid receiving relationship with a second bibulous member. Conditions are chosen wherein the liquid medium traverses the first bibulous member and at least a portion of the second bibulous member by capillary action. Determination of a border on the second bibulous member is made. The position of the border is related to the amount of analyte in the solution or the amount of reagent on the first bibulous member or the amount of the component in the liquid medium. By way of example, the analyte can be a drug, the reagent can be an antibody for the drug, and the component can be an enzyme labeled drug analog.

In another approach a combination is provided in a first liquid medium. The combination comprises (1) a first bibulous member and (2) an analyte, wherein a reagent for the analyte is present in the medium or on the first bibulous member. The first bibulous member is in liquid receiving relationship with an absorbent member. Conditions are chosen wherein the first medium flows through the first bibulous member and at least a portion of the absorbent member by capillary action and the reagent and usually the analyte become non-diffusively bound to the bibulous member. Thus, the first liquid medium can be contacted with all of the first member at once to achieve flow through or the first liquid medium can be contacted with only a portion of the first bibulous member. In the latter case the medium will traverse the remainder of the member by capillary action. The liquid receiving relationship between the bibulous member and the absorbent member is then terminated. A combination is provided, in a second liquid medium, comprising a portion of the first bibulous member and a component interreactive with the reagent, the first bibulous member being in liquid receiving relationship with a second bibulous member. Conditions are chosen such that the second medium traverses the first bibulous member and at least a portion of the second bibulous member by capillary action, with the proviso that the first bibulous member is in liquid receiving relationship with the absorbent member and the second bibulous member at substantially different times. Next, a border is determined on the second bibulous member. The position of the border is related to the amount of analyte in the first medium, or the amount of reagent, or the amount of the component in the second liquid medium.

In another aspect of the present invention the method comprises causing a reagent such as an sbp member in a first liquid medium or solution to become bound to a first bibulous member by contacting the first bibulous member with the medium. The first bibulous member is in liquid receiving relationship with an absorbent member. Conditions are chosen such that the first medium traverses or flows through the first bibulous member and at least a portion of the absorbent member by capillary action. The function of the first bibulous member is to bind the reagent quantitatively and tightly. The reagent must be bound in a defined or predetermined amount depending on the predetermined minimum detectible amount of analyte of interest. In general, the reagent bound will be no more than 20 fold less or 20 fold greater than the amount of analyte or component that traverses the first bibulous member. Frequently, all of the reagent in the first medium or solution will become bound.

In one approach in the present invention, a combination is provided in a first liquid, usually aqueous, medium or solution. The combination includes (1) a first bibulous member, a portion of which has a first reagent such as an sbp member non-diffusively bound to it, and (2) a sample suspected of containing an analyte. When the analyte is not capable of binding to the first reagent, a second reagent capable of binding to the analyte and to first reagent is present in the medium or on the first bibulous member.

A combination can be formed in one of a number of orders. For example, the first bibulous member can have the first reagent bound thereto. A portion of the first bibulous member ("contact portion") is contacted with the first medium or solution containing the analyte. Where the sample is an aqueous medium containing the analyte, the sample can account for some or all of the first medium or solution. The primary consideration is that a combination be provided, in a first medium, of the sample and the first reagent on a portion of a first bibulous member, for example, a strip, and either flowing through or traversing the member through capillary action. This movement can be upward, downward, horizontal, or combinations thereof. The movement of the first medium along or through the first bibulous member can be driven by the absorbent member in liquid receiving relationship with the first bibulous member. Such a driving or wicking type action provides for better control of the liquid contacting the chemically active part of the first bibulous member.

When the analyte is not capable of binding to the first reagent, a second reagent capable of binding to the analyte (as distinguished from being already bound to the analyte) and the first reagent is present in the first medium or solution or on the first bibulous member. If the second reagent is on the first bibulous member, it is generally diffusively bound so that contact with the aqueous medium will allow the second reagent to diffuse into the first medium. This diffusion can take place during the movement along the first bibulous member by the first medium.

The second reagent, as mentioned above, has the characteristic of binding to the analyte and to the first reagent. Where the analyte and the first reagent are the same or analogous, the second reagent can be a binding partner, such as an sbp member, for the arialyre or the analyte analog. However, the first sbp member can be other than an arialyre or an analyte analog. The function of the first reagent is to either bind the analyte or a second reagent in relation to the amount of analyte in the sample. Accordingly, where the first reagent does not bind the analyte or an analyte analog, the first reagent can be chosen to be a binding partner to the second reagent. In this circumstance, the second reagent will have two parts, one part, for example, a second sbp member, capable of binding to the analyte, and one part, for example, a third sbp member, capable of binding to the first reagent. The part capable of binding to the analyte can be complementary to the arialyre such as, for example, an sbp member for the analyte, such as an antibody. The other part of the second reagent can be a small organic molecule of a molecular weight less than 1500, and preferably greater than 250. The first reagent in this situation can be an sbp member that is complementary to either the part complementary to the analyte or the small organic molecule. Thus, the first reagent can be, for example, an antibody for an antibody, or an antibody for the small organic molecule. Exemplary small organic molecules are biotin, fluorescein, LSD, morphine, benzoylecgonine, and the like.

The amount of the second reagent that becomes bound to the bibulous member is related to the presence in the sample of the corresponding analyte in an amount at or exceeding a predetermined minimum detectible amount of that analyte. This minimum detectible amount is generally that amount above which the analyte is considered to be present. For example, for a drug one may be interested in only whether the drug is present in a certain concentration range. Although the drug might be present below that range in the sample or test solution, it would not be considered present because its concentration is not at or above the minimum detectible amount.

The aqueous medium or solution and the liquid medium may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent. Under some circumstances depending on the nature of the sample, some or all of the aqueous medium could be provided by the sample itself. Under certain circumstances, a non-aqueous solution or liquid medium can be employed using a polar or non-polar organic solvent. Such a circumstance can be, for example, where water is not necessary for reaction of the materials in an assay or where water would be detrimental to the activity of such materials.

When the aqueous medium is used, the pH for the medium will usually be in the range of 4–11, more usually 5–10, and preferably in the range of about 6–9. The pH is chosen that will facilitate the interfaction involved in the assay such as, for example, to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

It may be desirable in some instances to include from about 0.05 to 0.5 weight percent of a non-ionic detergent with the sample. Various polyoxyalkylene compounds may be employed of from about 200 to 20,000 daltons.

Moderate, and desirably substantially constant, temperatures are normally employed for carrying out the assay. The temperatures for the assay and production of a detectable signal will generally be in the range of about 4°–50° C., more usually in the range of about 10°–40° C., and frequently will be ambient temperatures, that is, about 15°–25° C.

The concentration in the first aqueous medium or solution of the component or the analyte that may be assayed will generally vary from about $10^{-4}$ to about $10^{-15}$M, more usually from about $10^{-6}$ to $10^{-14}$ M. Considerations, such as the concentration of the component or analyte of interest and the protocol will normally determine the concentration of the other reagents.

While the concentrations of many of the various reagents in the sample and reagent solutions will generally be determined by the concentration range of interest of the component and/or the analyte, the final concentration of at least some of the reagents will normally be determined empirically to optimize the sensitivity of the assay over the range of interest. With certain protocols, individual reagents may be used in substantial excess without detrimentally affecting the sensitivity of the assay.

When a strip is employed as the first bibulous member, the size of the strip is dependent on several considerations. The primary consideration is to capture a sufficient amount of analyte or reagent or component so that a sufficient signal will subsequently be obtained to achieve a sensitive and accurate assay. In that respect, the qualitative aspect of the present invention provides for increased sensitivity because analyte or reagent can be concentrated on a first bibulous member to fill all available binding sites by flowing a medium through such member into an absorbent member prior to bringing the first member into liquid reserving relationship with the second bibulous member. In general, for upward flow strips the fluid retention volume will be usually greater than 1 $\mu$L, preferably at least 5–200 $\mu$L. For downward flow strips retention volumes as low as 1–20 $\mu$L can be used but volumes of 5–200 $\mu$L are preferable.

Thickness of the strips is not critical and will normally be 0.05–2 mm, usually 0.1–1 mm, preferably 0.2–0.7 mm. Generally the minimum thickness is dictated by the strength of the material and the need to produce a readily detectible signal whereas the maximum width will be dictated by convenience of handling and cost of the reagents.

To permit conservation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The length of the strip will depend on the concentration of the analyte or the component or the reagent and practical considerations such as ease of handling and the number of situses on the strip and will be about 0.5 cm to 40 cm, usually about 1 cm to 25 cm, preferably about 4 to 20 cm but may be of any practical length. The structure of the strip can be varied widely and includes fine, medium fine, medium, medium coarse and coarse. In general, smaller pore size and finer material will provide slow capillary flow and efficient capture of the desired reagent on the strip. Courser more porous materials provide faster flow, but the efficiency of capture is reduced. Selection of the porosity of the material depends on the rate of binding of the components for a given assay. Preferably, the pore size should not be so small as to restrict flow and not be so large as to occlude serum, if serum is the sample of interest. Such a situation allows for one of the benefits of the present invention, namely, avoiding the necessity of a washing step.

The cross-sectional dimensions of the strip have been described in the preceding discussion in terms of a rectangle for the purpose of illustration and not limitation. As mentioned above, other shapes such as circular, triagonal, oval, etc, fall equally within the scope of this invention. The dimensions thereof can be determined by those skilled in the art with reference to the disclosure herein.

Other reagents, which are members of the detection system such as, e.g., the signal producing system, can vary widely in concentration depending upon the particular protocol and their role in signal production. Usually, the amount of a reagent, e.g., first sbp member, on the first bibulous member will be homogeneously or uniformly bound on at least a portion thereof between the contact portion and the absorbent member and is determined with reference to the predetermined minimum detectible amount of component or analyte. Usually, this amount will not exceed $10^4$ times the maximum amount of component or analyte to be assayed and will not be less than about equal the minimum amount of the reagent such as the first reagent used in the assay. The minimum concentration of the reagent is determined with reference to the minimum detectible amount of the component. This amount will depend on the sensitivity of detection and may vary from $10^{-19}$ mole to $10^{-6}$ mole usually $10^{-18}$ to $10^{-10}$ mole. Where the first reagent is employed to capture a second reagent, the amount of first reagent on the first bibulous member can be chosen such that only a predetermined amount of second reagent will become bound.

In carrying out an assay for an analyte, the protocol will usually involve forming a combination in an aqueous medium of the sample suspected of containing the analyte and the first reagent. The sample may be derived from a wide variety of sources, such as physiologic fluids, illustrated by saliva, blood, serum, plasma, urine, ocular lens fluid, spinal fluid, etc., food products such as milk and wine, chemical processing streams, food waste water, etc.

The contact portion of, or the entire, first bibulous member is contacted with the first medium, usually by immersion such as by dipping of the contact portion into the medium. However, contact of the first bibulous member with the first liquid medium or solution can be carried out by other techniques such as by spotting the first medium on the first bibulous member. This technique has particular application to a first bibulous member that is strip-like, circular, oval, sheet-like, etc. Wetting of the first bibulous member by capillary action usually is allowed to continue until a defined volume of medium has traversed the bibulous member. Commonly, at least 20 $\mu$L, usually at least 50 $\mu$L, frequently at least 100 $\mu$L, of the first medium will traverse the bibulous member. The upward limit of first medium traversing the bibulous member is generally determined by practical considerations such as the size of the device, and the like.

As a practical matter, relatively short times are desired for the first medium to traverse the first bibulous member. Usually, the traverse of the first medium over the first bibulous member will take at least 30 sec and not more than 1 hour, more usually from about 1 min to 30 minutes, but periods as long as 24 hours can be used.

After the first medium has traversed the first bibulous member and at least a portion of the absorbent member, or after contact of the entire first bibulous member with the first medium, the first bibulous member is brought into liquid receiving relationship with a second bibulous member. In a preferred embodiment the first bibulous member is in liquid receiving relationship with the absorbent member and a chromatographic member that will allow liquid flow by capillary action, such as the immunochromatographic member, at substantially different times. More preferably, the liquid receiving relationship between the first bibulous member and the absorbent member is terminated prior to instituting the liquid receiving relationship between the second bibulous member and the second medium. The relationship between the first bibulous member and the absorbent member on the one hand and the second bibulous member on the other hand may be instituted or terminated by physical or mechanical means or a combination thereof.

A portion of the second bibulous member is contacted with a second liquid, usually aqueous, medium. The second medium traverses the first bibulous member and at least a portion of the second bibulous member by capillary action. A component in the second medium becomes non-diffusively bound to the second bibulous member in relation to the presence of analyte in the first medium. The second bibulous member may have bound to it a detection agent.

The methods of the present invention can provide either a qualitative result or a quantitative determination of an analyte, a reagent, or a component. For a qualitative result in the present invention, a liquid receiving relationship between the first bibulous member and the second bibulous member is established only after the component or analyte has been concentrated on the first bibulous member. For a quantitative determination, the second bibulous member can be a chromatographic member such as an immunochromatographic member. In one embodiment where a reagent is employed, the component can be, for example, a conjugate of an enzyme and an analyte analog. Depending on the presence or amount of analyte in the sample, the component will become bound to reagent non-diffusively bound to the first bibulous member. If analyte is present in the sample above a minimum detectible amount, the amount of reagent is chosen such that a proportional amount of component will not bind to the first bibulous member but rather traverse to the second bibulous member. In some instances the second bibulous member may contain a binding partner for the component. In the instance where the component is an enzyme labeled analyte analog, this binding partner may bind to the enzyme portion of the conjugate or to the analyte analog portion of the conjugate. Accordingly, this binding partner can be an antibody for the enzyme or an antibody for the analyte analog. The component can include a label, or be capable of binding to a label. The binding partner on the second bibulous member can be a receptor for an antibody, for example, protein A in the circumstance where the first reagent is an antigen specific for immunoglobulin analyte.

Examples of immunochromatographic methods are described in U.S. Pat. Nos. 4,168,146 and 4,435,504, the disclosures of which are incorporated herein by reference in their entirety. As applied to the present invention, the component in the second aqueous medium will traverse the immunosorbing zone of the immunochromatographic member, being carried along with the liquid from the first bibulous member. The component becomes bound to the second bibulous member through, for example, the intermediacy of sbp member complex formation. For a qualitative result the immunosorbing zone can be a narrow band or small situs, which will provide an indication of the presence or absence of the analyte in the sample. The portion of the second bibulous member traversed by the second medium depends on the particular protocol involved but will preferably be the entire bibulous member. However, as a general rule, for both qualitative and quantitative determinations, the medium will traverse the portion of the second bibulous member at least through the immunosorbing zone. The dimensions of the second bibulous member can be determined according to the same considerations as those described above for the first bibulous member. The relationship of the size of the immunosorbing zone to the remainder of the second bibulous member is such that a sufficient amount of component can be passed through the immunosorbing zone in order to realize an accurate assay.

In a qualitative assay, following the traversal of the first and second bibulous members by the second medium, the presence of the component on or bound to the second bibulous member is determined. The presence of the component on the second bibulous member is related to the amount of analyte in the sample. Where the component contains a label, the second bibulous member can be examined for the presence of a detectible signal. If the signal is the result of a radioactive label, or the like, the signal can be detected directly at the second bibulous member. Where chemical agents form part of the signal producing means that includes the label, the contact portion of the first bibulous member can be dipped into, or otherwise contacted with, a developer solution containing remaining members of the signal producing system. Where only a part of the second bibulous member is contacted, this developer solution is allowed to flow along the first bibulous member through the second bibulous member. Depending on the protocol, a washing step may or may not be utilized. Alternatively, the second bibulous member can be contacted directly with the developer solution, such as by total dipping, spraying, and the like.

Depending on the protocol, it may be desirable to first contact the second bibulous member with a developer solution and then subsequently contact the second bibulous member with any remaining members of the signal producing system not present in the developer solution or the first and second mediums or present on the first or second bibulous members.

Generally, a sufficient time is allowed to elapse prior to measuring the signal to produce an amount of the signal producing compound required to define the region of the second bibulous member in which the component is found or bound. Once the detectible signal has been produced, the presence or absence of the analyte or the amount of analyte in the sample and/or the amount of reagent or component is known. For quantitative determinations, the signal producing system provides the manner by which the area in the second bibulous member to which the analyte or component is found or bound may be distinguished from the area in which it is absent. In this way, the distance from a predetermined point on the chromatograph is a measure of the amount of analyte in the sample and/or the component or reagent. In one embodiment, the region of the second bibulous member traversed by the component is observable due to the production of a detectible signal substantially uniformly throughout the region in which the component is present.

In one particular embodiment of the present invention, an aqueous medium is prepared containing a sample suspected of containing an analyte and a first reagent, which is a conjugate of an antibody for the analyte and a small organic molecule. The aqueous medium is contacted with a contact portion of a bibulous strip having non-diffusively bound thereto either an antibody for the small organic molecule or an antibody that recognizes the antibody for the analyte. An end portion of a bibulous strip is in contact with an absorbent strip. The medium traverses the bibulous strip and part of the absorbent strip. The antibody on the bibulous strip captures the first reagent. If analyte is present in the aqueous medium, the analyte is captured by the antibody of the first reagent.

The liquid receiving relationship between the bibulous strip and the absorbent member is terminated and the bibulous strip is brought into liquid receiving relationship with a second bibulous strip. A second liquid medium containing a component which is an enzyme labeled analyte analog is brought into contact with the contact portion of the first bibulous strip. The second bibulous strip contains antibody that binds to either the analyte analog or enzyme portion of the second reagent or to the conjugate itself. The antibody on the second bibulous material is non-diffusively and uniformly bound to a substantial portion of the second bibulous strip to form an immunochromatograph. The second aqueous medium traverses the first bibulous strip and the second bibulous strip.

If analyte is present in the sample, the analyte occupies the binding sites on the antibody for the analyte that is bound to the first bibulous strip. Consequently, the enzyme labeled analyte analog does not bind to the occupied binding sites on the first bibulous member and thus migrates to the second bibulous strip where it is captured by the antibody on the second bibulous strip. The amounts of the first reagent and component employed, therefore, must be predetermined amounts based on the suspected concentration range of interest of the analyte. In a qualitative assay, if no analyte or an amount of analyte under a predetermined concentration of interest is in the sample, then the component all becomes bound to the first bibulous member so that no component will migrate to the second bibulous strip. However, if analyte is present in the sample, the component migrates to the second bibulous member in proportion to the amount of analyte in the sample. In a quantitative assay, provided amounts are selected such that at least some component will migrate to the second bibulous strip even when no analyte is present in the sample, the component will migrate a distance along the second bibulous member in proportion to the amount of analyte in the sample.

After the second liquid medium has traversed the first bibulous strip and the second bibulous strip, contact between the first bibulous member and the second aqueous medium is terminated. The second bibulous strip is then contacted with a developer solution in order to determine the location of enzyme conjugate bound to the second bibulous strip. To this end the first and second bibulous strips can be immersed in a developer solution or the second bibulous strip can be removed from liquid receiving relationship with the first bibulous strip and contacted with the developer solution, which contains the remaining members of the signal producing system. In such a way, the distance of migration of the component on the second bibulous strip is determined and is correlated with the amount of analyte in the sample for a quantitative result. This correlation may be the result of carrying out the above method on known samples to determine migration distances and comparing the migration distance in the unknown sample with known values in order to determine the amount of analyte present in the sample.

The developer solution can contain the remaining members of the signal producing system or some of the members of the signal producing system, for example, a second enzyme, can be present on the second bibulous strip. See, for example, U.S. patent application No. 602,297 filed Apr. 20, 1984 and U.S. patent application No. 733,013 filed May 10, 1985, the disclosures of which are incorporated herein by reference in their entirety.

In another embodiment of the present invention a first bibulous strip having an analyte analog bound to it is contacted at a contact portion with an aqueous medium containing a sample suspected of containing an analyte and an antibody for the analyte. The first bibulous strip is in liquid receiving relationship with an absorbent member, and the medium is allowed to traverse the first bibulous strip and a portion of the absorbent member. The liquid receiving relationship between the absorbent member and the first bibulous strip is terminated and the first bibulous strip is brought into liquid receiving relationship with a second bibulous strip. The contact portion of the first bibulous strip is brought into contact with a second aqueous medium containing an antibody-enzyme conjugate which binds to the antibody for the analyte. The second bibulous strip contains a receptor for an antibody for the analyte, for example, protein A.

If analyte is present in the sample, the analyte binds to its complementary antibody and, consequently, this complex does not become bound to the first bibulous strip. However, if analyte is not present in the sample or is present at or below a predetermined detectible amount, then antibody for the analyte binds to the analyte analog on the first bibulous member. When the first bibulous strip is contacted with the second aqueous medium containing the antibody-enzyme conjugate, the conjugate becomes bound to the first bibulous strip if antibody for analyte is bound. Depending upon the amount of antibody for analyte bound to the first bibulous member, which in turn is related to the amount of analyte present in the sample, an amount of the conjugate migrates to the second bibulous strip where it is captured by the receptor for antibody.

After the medium has traversed the first bibulous strip and the second bibulous strip, the second bibulous strip is treated as described above in the previous embodiment in order to determine enzyme activity on the second bibulous strip. Again, the distance of migration of the conjugate on the second bibulous strip is related to the amount of analyte in the sample.

In another embodiment, a first bibulous strip with a portion having antibody for analyte bound thereto is contacted with an aqueous medium containing the sample of interest. The sample is allowed to traverse the first bibulous member being assisted by capillary migration into an absorbent member in liquid receiving relationship with the first bibulous member. After the traversal has taken place, the liquid receiving relationship between the first bibulous member and the absorbent member is terminated, and the first bibulous member is brought into liquid receiving relationship with a second bibulous member having antibody for analyte bound thereto. The first bibulous member is then contacted with an aqueous medium containing enzyme labeled analyte analog. This second aqueous medium traverses the first bibulous member and the second bibulous member.

If analyte is present in the sample, the analyte binds to the first bibulous member in the first traversal and the antibody binding sites on the first bibulous member become occupied. Thus, when the second aqueous medium traverses the first bibulous member, the enzyme labeled analyte analog does not bind to the first bibulous member but rather migrates to the second bibulous member in direct relationship to the amount of analyte present in the sample. Again, the second bibulous member is treated to detect enzyme activity and to permit determination of the distance of migration, which is then related to the amount of analyte in the sample.

The present invention has application to a wide diversity of protocols for determining the presence and/or amount of one or more analytes in a sample. One example in accordance with the present invention is an sbp member in a first aqueous medium that is caused to become bound to a first bibulous member by contacting a portion of the bibulous member with the medium. The first bibulous member is in liquid receiving relationship with an absorbent member. The medium traverses the first bibulous member and at least a portion of the absorbent member by capillary action. Next, the first bibulous member is caused to come into liquid receiving -relationship with a second bibulous member. A component in a second aqueous medium is caused to become non-diffusively bound to a second bibulous member in relation to the presence of analyte in the first medium. A portion of the first bibulous member is contacted with the second aqueous medium under conditions wherein the second medium traverses the first bibulous member by capillary action and at least a portion of the second bibulous member. The presence of the component on at least a portion of, or the distance the component has migrated on, the second bibulous member is then determined to determine the presence and/or amount of analyte in the sample. Protocols such as those described in U.S. patent applications Ser. Nos. 904,595, filed Sep. 5, 1986; 928,233, filed Nov. 7, 1986; 928,771, filed Nov. 7, 1986, the disclosures of which are incorporated herein by reference in their entirety, can be modified in accordance with the present invention to determine one or more analytes in a sample.

In carrying out an assay for determining the amount of component, for example, a metal ion, or an analyte in a liquid, usually aqueous, medium, the protocol will generally involve forming a combination in a liquid medium of the component and a first bibulous member zone ("first zone"). The component of interest may be found in a wide variety of sources such as chemical processing streams, media containing pollutants, waste water, physiologic fluids, and so forth. The first zone contains a predetermined level of a reagent interreactive with the component, for example, a chelator for the metal ion, or an sbp member for an analyte, non-diffusively bound thereto. In one approach a contact portion of the first zone is contacted with the liquid medium. Wetting of the first zone by capillary action is allowed to continue until the medium and the component have traversed all of the first zone and migrated into a second bibulous member zone ("second zone"). The second zone can be part of the same bibulous member as said first zone provided, however, that the composition of reagents bound to the two zones are different. Alternatively, the second zone can be part of a separate bibulous member that is brought into contact with the first zone to allow the medium and the component to migrate into the second zone by capillary migration.

Next, the second zone is examined to determine the distances of migration of the medium and the component. Generally, this may be accomplished by contacting the zone with a detection agent unless the component is otherwise directly detectible or the detection agent is bound to the zone. The detection agent can be a developer solution such as that for providing an enzyme substrate where the component contains an enzyme such as in the case of an enzyme labeled ligand analog. Where the component is an inorganic molecule, the detection agent can be a substance or substance that interreacts with the component to produce a signal such as a color. For example, oxidation—reduction reactions can be employed having as one member thereof a component where the reaction results in the generation of a colored product.

The detection agent will frequently be present in an aqueous medium which is contacted with the second zone by, for example, dipping the second zone into the medium containing the detection agent, applying the medium containing the detection agent to the second zone such as by spraying and the like, and so forth.

Sufficient time is provided so that the appropriate interaction can take place to the extent necessary. The time will depend on the nature of the interaction such as chemical or physical, the interactivity of the molecules involved, and the like.

After the appropriate level of signal has developed, the distances of migration of the component into the second zone or the difference in the distances of migration of the medium and the component into the second zone can be measured. This distance or difference is related to the amount of the component in the liquid medium or the amount of reagent. For example, standard curves can be prepared utilizing known amounts of components and reagents and unknown amounts can be obtained by a comparison of the distance or difference referred to above with the standard curve.

In a qualitative assay following the traversal of the first and second bibulous members by the second medium, the distance the component has traversed the second bibulous member is determined and is related to the amount of analyte in the sample. Where the component contains a label, the distance traversed can be determined from the presence of a detectible signal in the traversed area. If the label is, for example, a fluorophore, the signal can be detected directly at the second bibulous member. Where detection agents form part of the signal producing means that includes the label, the detection agents may be bound to the second bibulous member or the member can be contacted with a solution of the developer agent.

In a quantitative assay, generally, a sufficient time is allowed to elapse prior to measuring the signal to produce an amount of the signal producing compound required to define the distance along the second bibulous member over which the component has traversed. Once the detectible signal has been produced, the amount of analyte in the sample or the amount of reagent or component can be determined. Thus, the distance between the furthest point of traversal of the medium and the furthest point of traversal of the component on the chromatograph is a measure of the amount of analyte in the sample, or of component, or of reagent. The region of the second bibulous member traversed by the component will usually be observed as a substantially uniform detectible signal throughout the region in which the component is present.

The present invention also includes devices for analyzing for the presence or amount of an analyte or a reagent or component of interest. Referring to FIG. 1, the devices comprise a first bibulous member (10), an absorbent member (18), and a second bibulous member (20). The first bibulous member is capable of being an alternating liquid receiving relationship with the absorbent member and the second bibulous member. In an alternate embodiment, the present devices further comprise a means for alternating the liquid receiving relationship. As mentioned above, this means can be physical or mechanical and may be automated or non-automated. In one embodiment of a device in accordance with the present invention, the second bibulous member is an immunochromatograph.

As a matter of convenience, the reagents and devices employed in the present invention can be provided in a kit in packaged combination in predetermined amounts for use in conducting the present method in assaying for an analyte in the sample. For example, a kit useful in the present method can comprise in packaged combination a device as described above and a component or a component and a first reagent, as described above. Where an enzyme is used as a label, the reagents can include enzyme labelled analyte analog and a developer solution, which can contain substrate for the enzyme or precursors therefor including any additional substrates, enzymes and cofactors and any reaction partner of the enzymic product required to provide the detectible chromophore or fluorophore. In addition, other additives, such as ancillary reagents, may be included, for example, stabilizers, buffers, and the like. The relative amounts of the various reagents may be varied widely to provide for concentrations in solution of the reagents which substantially optimize the sensitivity of the assay. One or more of the reagents can be provided as dry powders, usually lyophilized, including excipients, which on dissolution will provide for a reagent solution having the appropriate concentrations for performing the assay. Each reagent can be packaged in separate containers or some reagents can be combined in one container where reactivity and shelf life will permit.

EXAMPLES

The invention is demonstrated further by the following illustrative examples. Parts and percentages are by weight to volume unless indicated otherwise.

EXAMPLE I

Definitions

PVA—polyvinyl alcohol

MES buffer—2-morpholinoethane sulfonic acid
TNBS—trinitrobenzenesulfonic acid
HEPES buffer—hydroxyethylpiperazine ethanesulfonic acid
DMF—dimethylformamide
PBS—phosphate buffered saline-10 mM sodium phosphate, 150 mM sodium chloride, pH 7
NHS—N-hydroxysuccinimide
Ig—immunoglobulins
IgG—immunoglobulin G

Materials

Nitrocellulose membrane (12 μ pore size) was obtained from Schleicher and Schuell. Affinity purified rabbit anti-Mouse Ig was obtained from Zymed. Glutaraldehyde (25% aqueous) was obtained from Sigma. Bovine IgG was obtained from Miles Diagnostics. Monoclonal anti-fluorescein 11H7 and monoclonal anti-digoxin 2H6 were prepared according to standard methods [Galfre, et al., Nature (1977) 266:550], using fluorescein-labeled bovine IgG and digoxin-labeled keyhole limpet hemocyanin, respectively, as immunogens. Phosphate buffer was 0.1M sodium phosphate, 0.2M sodium chloride, pH 7.3 Sodium sulfate buffer was phosphate buffer which additionally contained 9% w/w sodium sulfate. Horseradish peroxidase (HRP) was obtained from Shinko American. Blotting paper was obtained from Bio-Rad (Cat. No. 1650921). Carboxyfluorescein was from Kodak.

Preparation of Immobilized Anti-Fluorescein

Nitrocellulose membrane (7.5×9 cm) was incubated with 50 mL of a solution of 40 μg/mL rabbit anti-mouse Ig and 1 mg/mL bovine IgG in sodium sulfate buffer for 30 min. The membrane was washed with 50 mL of sodium sulfate buffer for 15 min., then fixed by incubating with 50 mL of 62 μg/mL glutaraldehyde in sodium sulfate buffer for 2 hr. The membrane was washed twice, for 15 min each, with 50 mL phosphate buffer, then incubated with 50 mL of 100 μg/mL monoclonal anti-fluorescein 11H7 and 1 mg/mL bovine IgG in phosphate buffer for 1 hr. The membrane was washed with 50 mL phosphate buffer for 15 min, washed with 50 mL deionized water for 15 min, and incubated with 50 mL of 0.2 mg/mL 20/30 PVA. The membrane was then dried at 50° C. for 15 min.

Preparation of Immobilized Anti-Digoxin

Nitrocellulose membrane (27.5×9 cm) was laminated onto 3-mil vinyl acetate film using 3M 9460 transfer adhesive and then incubated with 250 mL of a solution of 1 μg/mL rabbit anti-mouse Ig and 1 mg/mL bovine IgG in sodium sulfate buffer for 30 min. The membrane was washed with 250 mL of sodium sulfate buffer for 15 min, then fixed by incubating with 250 mL of 62 μg/mL glutaraldehyde in sodium sulfate buffer for 2 hr. The membrane was washed twice, for 15 min each, with 250 mL phosphate buffer, then incubated with 250 mL of 1 μg/mL monoclonal anti-digoxin 2H6 and 1 mg/mL bovine IgG in phosphate buffer for 1 hr. The membrane was washed with 250 mL phosphate buffer for 15 min, washed with 250 mL deionized water for 15 min, and incubated with 250 mL of 0.2 mg/mL 20/30 PVA. The membrane was then dried at 50° C. for 15 min.

Preparation of Blocked Nitrocellulose Membrane

Nitrocellulose membrane (7.5×9 cm) was incubated with 50 mL of a solution of 1 mg/mL bovine IgG in sodium sulfate buffer for 30 min. The membrane was washed with 50 mL of sodium sulfate buffer for 15 min, then fixed by incubating with 50 mL of 62 μg/mL glutaraldehyde in sodium sulfate buffer for 2 hr. The membrane was washed twice, for 15 min each, with 50 mL phosphate buffer, then incubated with 50 mL of 1 mg/mL bovine IgG in phosphate buffer for 1 hr. The membrane was washed with 50 mL phosphate buffer for 15 min, washed with 50 mL deionized water for 15 min, and incubated with 50 mL of 0.2 mg/mL 20/30 PVA. The membrane was then dried at 50° C. for 15 min.

Preparation of Digoxin-labeled HRP

Ethylenediamine (3M, pH 5.0; 3.33 mL), and 1-(3-dimethylaminopropyl)-3-ethylcarbodiimide (1M, 0.1 mL) were added to a solution of HRP (50 mg in 6.6 mL of 138 mM MES buffer, pH 5.0), and the mixture was stored at room temperature for 15 hr. The resulting aminated HRP was purified by chromatography on Sephadex G-25 using 0.02% aqueous sodium azide as eluant, and was found to have an average of 11 amino groups per HRP (TNBS titration). Aminated HRP (37.9 mg) in HEPES buffer(200 mM, pH 8.0; 7 mL) was treated with three 95 μL-portions of succinic anhydride (2M in DMF) added at 10 min intervals, and 5 min after each addition a 190-μL portion of 1M sodium hydroxide was added to maintain the pH at 8. The succinylated aminated HRP was purified by chromatography on Sephadex G-25 using 0.02% aqueous sodium azide as eluant. The succinylated aminated HRP was reaminated by treating the material (30.8 mg) in MES buffer (70 mM, pH 5.0; 4.1 mL) with ethylenediamine (3M, pH 5.0; 2.07 mL) and 1-(3-dimethylaminopropyl)-3-ethylcarbodiimide (1M, 0.062 mL) for 6 hr at room temperature. The reaminated HRP was purified by chromatography on Sephadex G-25 using 0.02% aqueous sodium azide as eluant and was found to have 15.5 amino groups per HRP (TNBS titration). The reaminated HRP (2 mg/mL in PBS, pH 7.0) was reacted with a 200-fold excess of the NHS ester of 3-digoxigenin-0-carboxymethyloxime and then exhaustively dialyzed. The resulting digoxin-labeled HRP had 12 digoxins/HRP (based on titration of residual amino groups with TNBS).

Preparation of Fluorescein-labeled Anti-Digoxin 2H6

Monoclonal anti-digoxin 2H6 (7.3 mg/mL, 0.2 mL) in phosphate buffer was treated with the NHS ester of 6-carboxyfluorescein (20 mM in DMF; 5 μL) and incubated for 5 min at room temperature, then 16 hr at 4° C. the fluorescein-labeled anti-digoxin was purified by chromotography on Sephadex G-25 using phosphate buffer as eluant, and was found to have 3.6 fluoresceins per antibody.

Device. (Refer to FIG. 1)

First bibulous member (10)—an end portion, consisting of a 6 mm×6 mm piece of blocked nitrocellulose membrane (12), and a capture pad, consisting of a 6 mm×10 mm piece of immobilized anti-fluorescein (14), were laminated onto 3-mil acetate film (16) such that the two sections overlapped by 1 mm.

Absorbent member (18)—a 12 mm×50 mm strip of blotting paper Second bibulous member (20) (quantitating strip)—a 6 mm×90 mm strip of immobilized anti-digoxin.

During the assay the first bibulous member was first in liquid receiving relationship (overlap by 1 mm) with the absorbent member (referred to below as the sample uptake step) and then in liquid receiving relationship with the second bibulous member (referred to below as the quantitation step).

Assay Protocol

The assay was carried out in two steps—a sample uptake step and a quantitation step. For the sample uptake step, sample (100 μL) and fluorescein-labeled anti-digoxin 2H6 (1.25 μg/mL, 50 μL) were dispensed into the bottom of a 16×100 mm test tube and mixed. An end portion of the first bibulous member of an assay device such as that depicted in FIG. 1 was placed in the test tube and the liquid was allowed to wick along the first bibulous member and into the absorbent. After all of the liquid had been taken up by the device, the contact between absorbent and the first bibulous member was terminated. For the quantitation step, the quantitating strip was placed in contact with the upper edge of the capture pad. The end portion of the first bibulous member of the assay device was then placed in a test tube containing digoxin-labeled HRP (250 ng/mL, 100 μL) and liquid was allowed to pass through the capture pad into the quantitating strip until the quantitating strip was filled with liquid. The quantitating strip was then removed from the device and placed in a developer solution (containing 0.5 mg/mL dicarboxidine, 10 mM hydrogen peroxide in 100 mM sodium citrate, pH 5.0) until a blue color had developed on a portion of the quantitating strip. The length (migration height) of the blue area was measured and was related to the concentration of digoxin in the sample.

Assay Results

A series of assays was performed using serum samples containing known concentrations of digoxin (Column Digoxin calibrators, Syva Company). The results are summarized in Table 1.

TABLE 1

| Digoxin Concentration (ng/mL) | Migration Height (mm) |
| --- | --- |
| 0 | 20 |
| 0.5 | 24 |
| 1 | 29 |
| 2 | 39 |
| 3 | 48 |
| 4 | 55 |

The above results indicate that an accurate and sensitive assay for digoxin can be conducted utilizing the method and devices of the present invention. Increasing concentrations of digoxin resulted in greater migration height observed on the quantitating strip.

EXAMPLE 2

Measurement of Concentration of Digoxin-Labeled HRP

Using devices as described above in Example 1, 100 μl of a 400 ng/ml solution of fluorescein-labeled anti-digoxin was passed by capillary action through the first bibulous member into the absorbent. Solutions of digoxin-labeled HRP of varying concentrations were analyzed with this device by passing them by capillary action through the first bibulous member into the second bibulous member. The migration distances were a function of the concentration of digoxin-labeled HRP as shown in the following table (Table 2).

TABLE 2

| Concentration of Digoxin-Labeled HRP (ng/mL) | Migration Distance (mm) |
| --- | --- |
| 100 | 0 |
| 150 | 7 |
| 200 | 14 |
| 250 | 18 |
| 300 | 23 |

EXAMPLE 3

Measurement of Concentration of Fluorescein-Labeled Anti-Digoxin

Using devices as described above in Example 1, 120 μl of solutions of fluorescein-labeled anti-digoxin of varying concentrations were passed by capillary action through the first bibulous member into the absorbent. The analyses were completed by passing solutions of 275 ng/ml digoxin-labeled HRP through the first bibulous member into the second bibulous member by capillary action. The migration distances were a function of the fluorescein-labeled anti-digoxin concentrations as shown in the following table (Table 3).

TABLE 3

| Concentration of Fluorescein-Labeled Anti-Digoxin (ng/mL) | Migration Distance (mm) |
| --- | --- |
| 660 | 35 |
| 1000 | 20 |

EXAMPLE 4

Measurement Of Magnesium Chloride Concentration

Devices are prepared in accordance with FIG. 1 where the second bibulous members are pieces (0.5×10 cm) of untreated nitrocellulose membrane (12 μ pore size). The first bibulous member (0.5×1.0 cm) are prepared by treating Whatman 1C chromatography paper sequentially with carbonyl diimidazole (R. F. Zuk, V. K. Ginsberg, T. Houts, et al. (1986) *Clin Chem*, 31:1144–1150), ethylenediamine, and the anhydride of diethylenetriaminepentaacetic acid in methylene chloride. The members are dried, washed repeatedly with water, and redtied.

Using these devices, aqueous solutions of varying magnesium chloride concentration are passed through the first bibulous member into the second bibulous member by capillary action. Magnesium ion is taken up by the chelating group on the first bibulous member. The magnesium chloride-containing zones on the second bibulous member are visualized by spraying the strips with a dilute solution of Eriochrome Black T buffered at pH 9. The migration distances are a function of the magnesium chloride concentration.

EXAMPLE 5

Measurement of Sodium Iodate Concentration

The first bibulous member of devices similar to those of the preceding example are treated with excess aqueous ferrous chloride and then washed and dried. Aqueous solutions of sodium iodate of varying concentrations are passed through the first bibulous member by capillary action into the second bibulous member. Sodium iodate is reduced to sodium iodide by the chelated ferrous ion. After the second bibulous member has filled with liquid, the unreduced sodium iodate-containing zones are visualized by contacting the second bibulous member with a developer solution containing starch and sodium iodide. The migration distances are a function of the sodium iodate concentration.

EXAMPLE 6

Measurement of Ferrous Chloride Concentration

Using devices similar to those described in Example 4, 50 µl of aqueous ferrous chloride solutions of varying concentrations are passed through the first bibulous member by capillary action into the absorbent strips. Solutions of 0.10 mM sodium iodate are then passed through the first bibulous member by capillary action into the second bibulous member. The unreduced sodium iodate-containing zone on the second bibulous member is visualized as in the previous example. The migration distances are a function of the ferrous chloride concentration.

EXAMPLE 7

Alternate Method for Measurement of Ferrous Chloride Concentration

The procedure described above in Example 6 for the measurement of ferrous chloride concentration is followed, except that 5 µl samples of the aqueous ferrous chloride solution are applied directly to the first bibulous member rather than passing them through the first bibulous member. The migration distances are a function of the ferrous chloride concentration.

Although the foregoing invention has been described in some detail by way of illustration and example for purposes of clarity and understanding, it will be obvious that certain changes and modifications may be practiced within the scope of the appended claims.

What is claimed is:

1. A method for conducting an assay for the determination of an analyte, a component, or a reagent, which method comprises:

providing in combination (1) a first bibulous member zone ("first zone") having a reagent non-diffusively bound thereto with the proviso that when an analyte is to be detected, said reagent becomes bound to the first zone in relation to the amount of analyte present, and (2) a liquid medium containing a component that is interreactive with said reagent, under conditions wherein said liquid medium and at least a portion of said component contained therein traverse all of said first zone and migrate by capillary migration into a second bibulous member zone ("second zone"), of different composition than said first zone and incapable of specifically binding said component except when an analyte is to be detected; and determining the distance said component has migrated into said second zone or the difference in the distances said medium and said component have migrated into said second zone, said distance or said difference being related to the amount of said analyte or said component in said liquid medium or the amount of said reagent.

2. The method of claim 1 wherein prior to providing said combination said reagent is caused to non-diffusively bind to said first zone by contacting said first zone with a solution containing said reagent, and said difference or said distance is related to the amount of said reagent that binds to said first zone.

3. The method of claim 2 wherein said amount of said reagent is related to the amount of an analyte in said solution of said reagent.

4. The method of claim 1 wherein said first zone and said second zone are integral to a single bibulous member.

5. The method of claim 1 wherein said first zone is integral to a first bibulous member and said second zone is integral to a second bibulous member and said first zone is brought into liquid receiving relationship with said second zone during said assay and prior to providing said combination.

6. The method of claim 1 wherein said component and said reagent are each a member of a specific binding pair.

7. The method of claim 1 wherein said component and said reagent are chemically interreactive.

8. The method of claim 1 wherein said determining the distance said component has migrated into said second zone involves an oxidation-reduction reaction.

9. The method of claim 1 wherein said component is an enzyme labeled ligand analog and said reagent is antibody for said ligand.

10. The method of claim 1 wherein the difference in the distances said medium and said component have migrated into said second zone is determined.

* * * * *